United States Patent
Schulman et al.

(10) Patent No.: US 6,208,894 B1
(45) Date of Patent: *Mar. 27, 2001

(54) SYSTEM OF IMPLANTABLE DEVICES FOR MONITORING AND/OR AFFECTING BODY PARAMETERS

(75) Inventors: Joseph H. Schulman, Santa Clarita; Carla M. Mann, Beverly Hills, both of CA (US)

(73) Assignee: Alfred E. Mann Foundation for Scientific Research and Advanced Bionics, Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/048,826

(22) Filed: Mar. 25, 1998

Related U.S. Application Data

(60) Provisional application No. 60/039,164, filed on Feb. 26, 1997.

(51) Int. Cl.$^7$ .......................................... A61N 1/00
(52) U.S. Cl. ............................ 607/2; 607/59; 600/300; 128/903
(58) Field of Search .................................. 600/300, 301, 600/508, 509, 16, 17; 607/30, 32, 59, 60, 2, 9, 17, 48, 50, 57, 62–65; 128/903, 898; 604/20, 21, 890.1, 891.1, 93

(56) References Cited

U.S. PATENT DOCUMENTS

| | | | |
|---|---|---|---|
| 4,041,954 | * | 8/1977 | Ohara . |
| 4,543,955 |   | 10/1985 | Schroeppel . |
| 4,888,064 |   | 12/1989 | Strandberg . |
| 4,925,443 | * | 5/1990 | Heilman et al. ........................ 600/16 |
| 5,113,859 |   | 5/1992 | Funke . |
| 5,113,869 | * | 5/1992 | Nappholz et al. . |
| 5,193,539 | * | 3/1993 | Schulman et al. ...................... 600/2 |
| 5,411,535 |   | 5/1995 | Fujii et al. . |
| 5,562,713 | * | 10/1996 | Silivian . |
| 5,694,952 |   | 12/1997 | Lidman et al. . |
| 5,725,559 | * | 3/1998 | Alt et al. . |
| 5,728,154 |   | 3/1998 | Crossett et al. . |
| 5,733,313 | * | 3/1998 | Barreras, Sr. et al. . |
| 5,759,199 | * | 6/1998 | Snell et al. ............................. 607/60 |

\* cited by examiner

Primary Examiner—Linda C. M. Dvorak
Assistant Examiner—Bryan K. Yarnell
(74) Attorney, Agent, or Firm—Freilich, Hornbaker & Rosen

(57) ABSTRACT

A system for monitoring and/or affecting parameters of a patient's body and more particularly to such a system comprised of a system control unit (SCU) and one or more other devices, preferably battery-powered, implanted in the patient's body, i.e., within the envelope defined by the patient's skin. Each such implanted device is configured to be monitored and/or controlled by the SCU via a wireless communication channel. In accordance with the invention, the SCU comprises a programmable unit capable of (1) transmitting commands to at least some of a plurality of implanted devices and (2) receiving data signal from at least some of those implanted devices. In accordance with a preferred embodiment, the system operates in closed loop fashion whereby the commands transmitted by the SCU are dependent, in part, on the content of the data signals received by the SCU. In accordance with the invention, a preferred SCU is similarly implemented as a device capable of being implanted beneath a patient's skin, preferably having an axial dimension of less than 60 mm and a lateral dimension of less than 6 mm. Wireless communication between the SCU and the implanted devices is preferably implemented via a modulated sound signal, AC magnetic field, RF signal, or electric conduction.

12 Claims, 14 Drawing Sheets

OPEN LOOP CONTROL/MONITOR

OPTIONAL USE OF
TRANSLATION TABLE

CLOSED LOOP CONTROL

EXEMPLARY INJURY

COORDINATED CLOSED LOOP HAND CONTROL

SYSTEM OF IMPLANTABLE DEVICES FOR MONITORING AND/OR AFFECTING BODY PARAMETERS

This application claims the benefit of U.S. Provisional Application Ser. No. 60/042,447 filed Mar. 27, 1997 and U.S. Patent Application Ser. No. 09/030,106 filed Feb. 25, 1998 entitled "Battery-Powered Patient Implantable Device" which in turn claims the benefit of U.S. Provisional Application Ser. No. 60/039,164 filed Feb. 26, 1997.

BACKGROUND OF THE INVENTION

The present invention relates to systems for monitoring and/or affecting parameters of a patient's body for the purpose of medical diagnosis and/or treatment. More particularly, systems in accordance with the invention are characterized by a plurality of devices, preferably battery-powered, configured for implanting within a patient's body, each device being configured to sense a body parameter, e.g., temperature, $O_2$ content, physical position, etc., and/or to affect a parameter, e.g., via nerve stimulation.

Applicants' parent application Ser. No. 09/030,106 entitled "Battery Powered Patient Implantable Device", incorporated herein by reference, describes devices configured for implantation within a patient's body, i.e., beneath a patient's skin, for performing various functions including: (1) stimulation of body tissue, (2) sensing of body parameters, and (3) communicating between implanted devices and devices external to a patient's body.

SUMMARY OF THE INVENTION

The present invention is directed to a system for monitoring and/or affecting parameters of a patient's body and more particularly to such a system comprised of a system control unit (SCU) and one or more devices implanted in the patient's body, i.e., within the envelope defined by the patient's skin. Each said implanted device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates in closed loop fashion whereby the commands transmitted by the SCU are dependent, in part, on the content of the data signals received by the SCU.

In accordance with a preferred embodiment, each implanted device is configured similarly to the devices described in Applicants' parent application 09/030,106 and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

In accordance with a significant aspect of the preferred embodiment, a preferred SCU is also implemented as a device capable of being injected into the patient's body. Wireless communication between the SCU and the other implanted devices can be implemented in various ways, e.g., via a modulated sound signal, AC magnetic field, RF signal, or electrical conduction.

In accordance with a further aspect of the invention, the SCU is remotely programmable, e.g., via wireless means, to interact with the implanted devices according to a treatment regimen. In accordance with a preferred embodiment, the SCU is preferably powered via an internal power source, e.g., a rechargeable battery. Accordingly, an SCU combined with one or more battery-powered implantable devices, such as those described in the parent application, form a self-sufficient system for treating a patient.

In accordance with a preferred embodiment, the SCU and other implanted devices are implemented substantially identically, being comprised of a sealed housing configured to be injected into the patient's body. Each housing contains sensor/stimulator circuitry for driving an input/output transducer, e.g., an electrode, to enable it to additionally operate as a sensor and/or stimulator.

Alternatively, the SCU could be implemented as an implantable but non-injectable housing which would permit it to be physically larger enabling it to accommodate larger, higher capacity components, e.g., battery, microcontroller, etc. As a further alternative, the SCU could be implemented in a housing configured for carrying on the patient's body outside of the skin defined envelope, e.g., in a wrist band.

In accordance with the invention, the commands transmitted by the SCU can be used to remotely configure the operation of the other implanted devices and/or to interrogate the status of those devices. For example, various operating parameters, e.g., the pulse frequency, pulse width, trigger delays, etc., of each implanted device can be controlled or specified in one or more commands addressably transmitted to the device. Similarly, the sensitivity of the sensor circuitry and/or the interrogation of a sensed parameter, e.g., battery status, can be remotely specified by the SCU.

In accordance with a significant feature of the preferred embodiment, the SCU and/or each implantable device includes a programmable memory for storing a set of default parameters. In the event of power loss, SCU failure, or any other catastrophic occurrence, all devices default to the safe harbor default parameters. The default parameters can be programmed differently depending upon the condition being treated. In accordance with a further feature, the system includes a switch preferably actuatable by an external DC magnetic field, for resetting the system to its default parameters.

In an exemplary use of a system in accordance with the present invention, a patient with nerve damage can have a damaged nerve "replaced" by an implanted SCU and one or more implanted sensors and stimulators, each of which contains its own internal power source. In this exemplary system, the SCU would monitor a first implanted sensor for a signal originating from the patient's brain and responsively transmit command signals to one or more stimulators implanted past the point of nerve damage. Furthermore, the SCU could monitor additional sensors to determine variations in body parameters and, in a closed loop manner, react to control the command signals to achieve the desired treatment regimen.

The novel features of the invention are set forth with particularity in the appended claims. The invention will be best understood from the following description when read in conjunction with the accompanying drawings.

DESCRIPTION OF THE PREFERRED EMBODIMENTS

The present invention is directed to a system for monitoring and/or affecting parameters of a patient's body and more particularly to such a system comprised of a system control unit (SCU) and one or more devices implanted in a patient's body, i.e., within the envelope defined by the patient's skin. Each such implantable device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates in closed loop fashion whereby the commands transmitted by the SCU are dependent, in part, on the content of the data signals received by the SCU.

In accordance with a preferred embodiment, each implanted device is configured similarly to the devices described in Applicants' parent application 09/030,106 and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Figure 1:
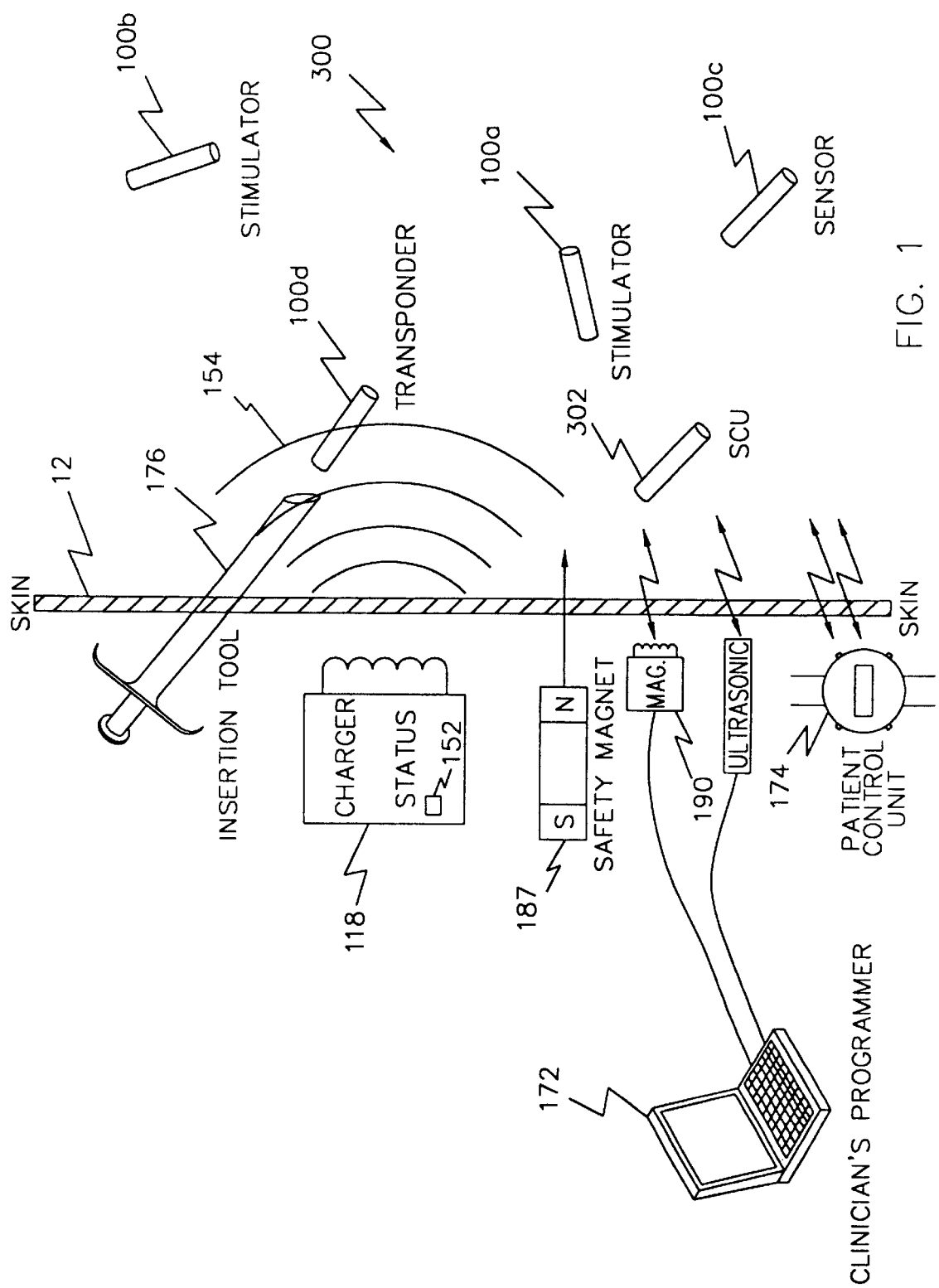
FIG. 1 is a simplified block diagram of the system of the present invention comprised of implanted devices, e.g., microstimulators, microsensors and microtransponders, under control of an implanted system control unit (SCU)
Figure 2:
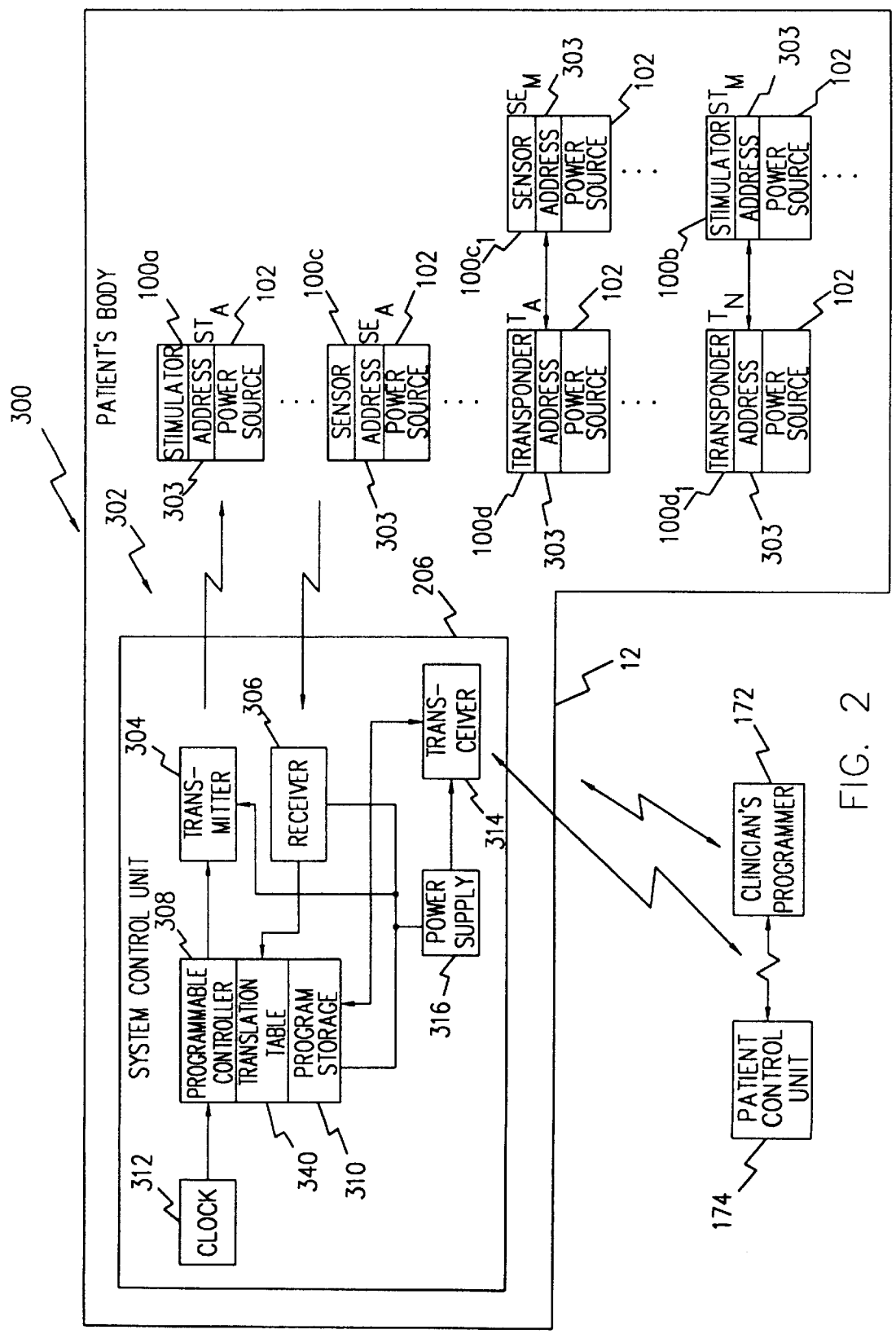
FIG. 2 comprises a block diagram of the system of FIG. 1 showing the functional elements that form the system control unit and implanted microstimulators, microsensors and microtransponders.

FIG. 1 (essentially corresponding to FIG. 2 of the parent application) and FIG. 2 show an exemplary system 300 made of implanted devices 100, preferably battery powered, under control of a system control unit (SCU) 302, preferably also implanted beneath a patient's skin 12. As described in the parent application, potential implanted devices 100 (see also the block diagram shown in FIG. 3A) include stimulators, e.g., 100a, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housing having an axial dimension of less than 60 mm and a lateral dimension of less than 6 mm. Accordingly, such stimulators, sensors and transponders are respectively referred to as microstimulators, microsensors, and microtransponders. Such microstimulators and microsensors can thus be positioned beneath the skin within a patient's body using a hypodermic type insertion tool 176.

As described in the parent application, microstimulators and microsensors are remotely programmed and interrogated via a wireless communication channel, e.g., modulated AC magnetic, sound (i.e., ultrasonic), RF or electric fields, typically originating from control devices external to the patient's body, e.g., a clinicians's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with an identification code (ID) 303 specified in address storage circuitry 108 (see FIG. 3A) as described in the parent application.

By using one or more such implantable devices in conjunction with the SCU 302 of the present invention, the capabilities of such implanted devices can be further expanded. For example, in an open loop mode (described below in reference to FIG. 5), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 7–9), the SCU 302 periodically interrogates one or more microsensors and accordingly adjust the commands transmitted to one or more microstimulators.

FIG. 2 shows the system 300 of the present invention comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the parent application in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferably that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock 312, preferably a real time clock that permits tasks to be scheduled at specified times of day.

The signal transmitter 304 and signal receiver 306 preferably communicate with implanted devices 100 using sound means, i.e., mechanical vibrations, using a transducer having a carrier frequency modulated by a command data signal. In a preferred embodiment, a carrier frequency of 100 KHz is used which corresponds to a frequency that freely passes through a typical body's fluids and tissues. However, such sound means that operate at any frequency, e.g., greater than 1 Hz, are also considered to be within the scope of the present invention. Alternatively, the signal transmitter 304 and signal receiver 306 can communicate using modulated AC magnetic, RF, or electric fields.

The clinician's programmer 172 and/or the patient control unit 174 and/or other external control devices can also communicate with the implanted devices 100, as described in the parent application, preferably using a modulated AC magnetic field. Alternatively, such external devices can communicate with the SCU 302 via a transceiver 314 coupled to the programmable controller 308. Since, in a preferred operating mode, the signal transmitter 304 and signal receiver 306 operate using sound means, a separate transceiver 314 which operates using magnetic means is used for communication with external devices. However, a single transmitter 304/receiver 306 can be used in place of transceiver 314 if a common communication means is used.

Figure 3A:
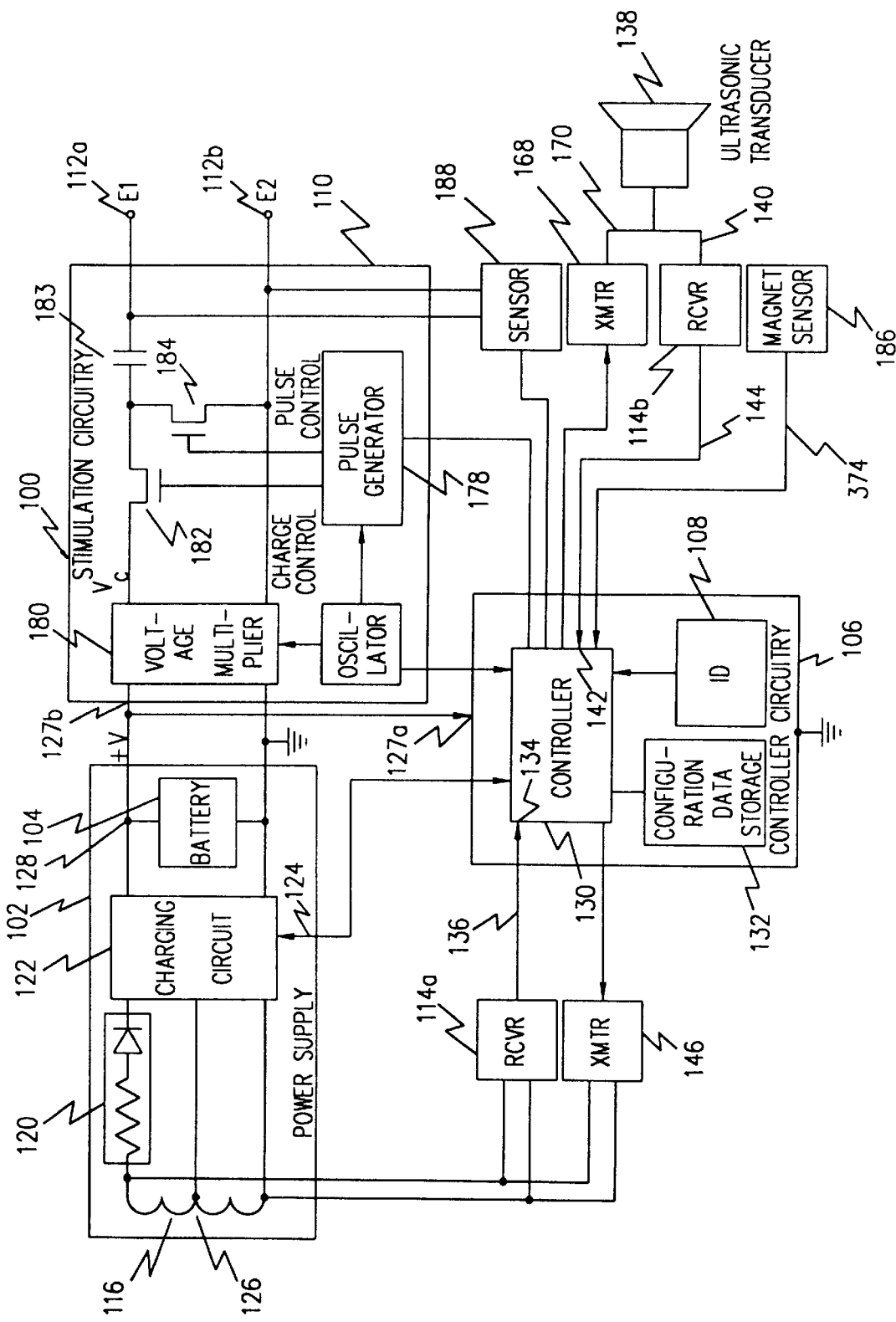
FIG. 3A comprises a block diagram of an exemplary implanted device, as shown in the parent application, including a battery for powering the device for a period of time in excess of one hour in response to a command from the system control unit.
Figure 3B:
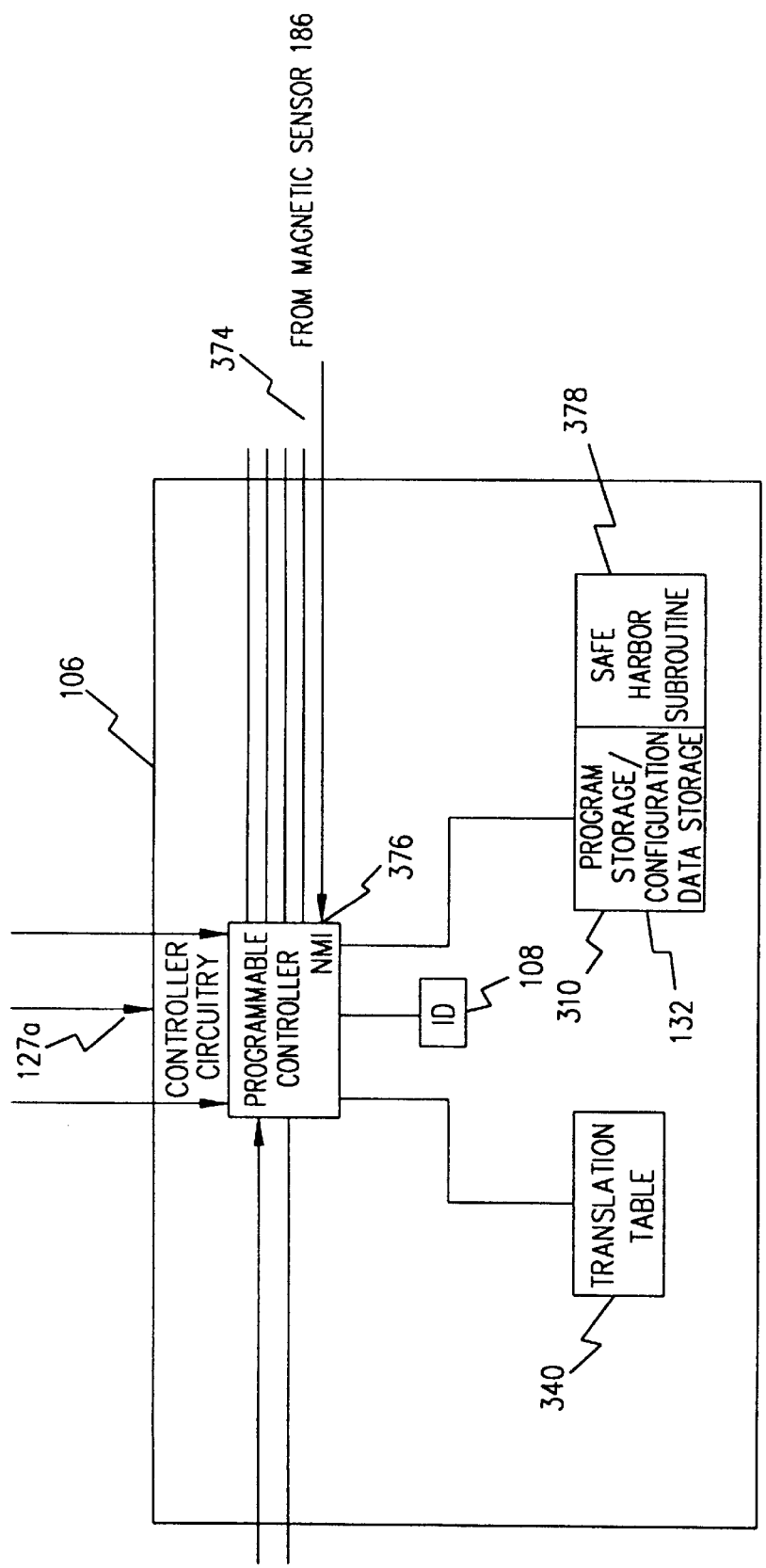
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implanted device 100 (as shown in FIG. 2 of the parent application) which includes a battery 104, preferably rechargeable, for powering the device for a period of time in excess of one hour and responsive to command signals from a remote device, e.g., the SCU 302. As described in the parent application, the implantable device 100 is preferably configurable to alternatively operate as a microstimulator and/or microsensor and/or microtransponder due to the commonality of most of the circuitry contained within. Such circuitry can be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable using sound means via transducer 138) and the RCVR 114a and XMTR 146 correspond to the transceiver 314 (preferably operable using magnetic means via coil 116).

In a preferred embodiment, the contents of the program storage 310, i.e., the software that controls the operation of the programmable controller 308, can be remotely downloaded, e.g., from the clinician's programmer 172 using data modulated onto an AC magnetic field. In this embodiment, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patient's could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316. While a primary battery, i.e., a nonrechargeable battery, is suitable for this function, it is preferable that the power supply 316 include a rechargeable battery, e.g., battery 104 as described in the parent application, that can be recharged via an AC magnetic field produced external to the patient's body. Accordingly, the power supply 102 of FIG. 3A (described in detail in the parent application) is the preferred power supply 316 for the SCU 302 as well.

The battery-powered devices 100 of the parent invention are preferably configurable to operate in a plurality of operation modes, e.g., via a communicated command signal. In a first operation mode, device 100 is remotely configured to be a microstimulator, e.g., 100a and 100b. In this embodiment, controller 130 stimulation circuitry 110 to generate a sequence of drive pulses through electrodes 112 to stimulate tissue, e.g., a nerve, proximate to the implanted location of the microstimulator, e.g., 100a or 100b. In operation, a programmable pulse generator 178 and voltage multiplier 180 are configured with parameters (see Table I) corresponding to a desired pulse sequence and specifying how much to multiply the battery voltage (e.g., by summing charged capacitors or similarly charged battery portions) to generate a desired compliance voltage $V_C$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby nerve. Alternatively, electrodes can be selected that will form an equivalent capacitor within the body tissue.

TABLE I

Stimulation Parameters

| | |
|---|---|
| Current | continuous current charging of storage capacitor |
| Charging currents | 1, 3, 10, 30, 100, 250, 500 µa |
| Current Range | 0.8 to 40 ma in nominally 3.2% steps |
| Compliance Voltage | selectable, 3–24 volts in 3 volt steps |
| Pulse Frequency (PPS) | 1 to 5000 PPS in nominally 30% steps |
| Pulse Width | 5 to 2000 µs in nominally 10% steps |
| Burst On Time (BON) | 1 ms to 24 hours in nominally 20% steps |
| Burst Off Time (BOF) | 1 ms to 24 hours in nominally 20% steps |
| Triggered Delay to BON | either selected BOF or pulse width |
| Burst Repeat Interval | 1 ms to 24 hours in nominally 20% steps |
| Ramp On Time | 0.1 to 100 seconds (1, 2, 5, 10 steps) |
| Ramp Off Time | 0.1 to 100 seconds (1, 2, 5, 10 steps) |

In a next operation mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID stored in address storage 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, or $O_2$ content and provided the sensed data to the controller circuitry 106. Preferably, the sensor circuitry includes a programmable bandpass filter and an analog to digital (A/D) converter that can sense and accordingly convert the voltage levels across the electrodes 112 into a digital quantity. Alternatively, the sensor circuitry can include one or more sense amplifiers to determine if the measured voltage exceeds a threshold voltage value or is within a specified voltage range. Furthermore, the sensor circuitry 188 can be configurable to include integration circuitry to further process the sensed voltage. The operation modes of the sensor circuitry 188 is remotely programable via the devices communication interface as shown below in Table II.

TABLE II

Sensing Parameters

| | |
|---|---|
| Input voltage range | 5 μv to 1 V |
| Bandpass filter rolloff | 24 dB |
| Low frequency cutoff choices | 3, 10, 30, 100, 300, 1000 Hz |
| High frequency cutoff choices | 3, 10, 30, 100, 300, 1000 Hz |
| Integrator frequency choices | 1 PPS to 100 PPS |
| Amplitude threshold for detection choices | 4 bits of resolution |

Additionally, the sensing capabilities of a microsensor include the capability to monitor the battery status via path 124 from the charging circuit 122 and can additionally include using the ultrasonic transducer 138 or the coil 116 to respectively measure the magnetic or ultrasonic signal magnitudes (or transit durations) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operation mode, the battery-powered implantable device 100 can be configured to operate as a microtransponder, e.g., 100d. In this operation mode, the microtransponder receives (via the aforementioned receiver means, e.g., AC magnetic, sonic, RF or electric) a first command signal from the SCU 302 and retransmits this signal (preferably after reformatting) to other implanted devices (e.g., microstimulators, microsensors, and/or microtransponders) using the aforementioned transmitter means (e.g., magnetic, sonic, RF or electric). While a microtransponder may receive one mode of command signal, e.g., magnetic, it may retransmit the signal in another mode, e.g., ultrasonic. For example, clinician's programmer 172 may emit a modulated magnetic signal using a magnetic emitter 190 to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic signal which can pass through the body with fewer restrictions. In another exemplary use, the patient control unit 174 may need to monitor a microsensor 100c in a patient's foot. Despite the efficiency of ultrasonic communication in a patient's body, an ultrasonic signal could still be insufficient to pass from a patient's foot to a patient's wrist (the typical location of the patient control unit 174). As such, a microtransponder 100d could be implanted in the patient's torso to improve the communication link.

Figure 4:
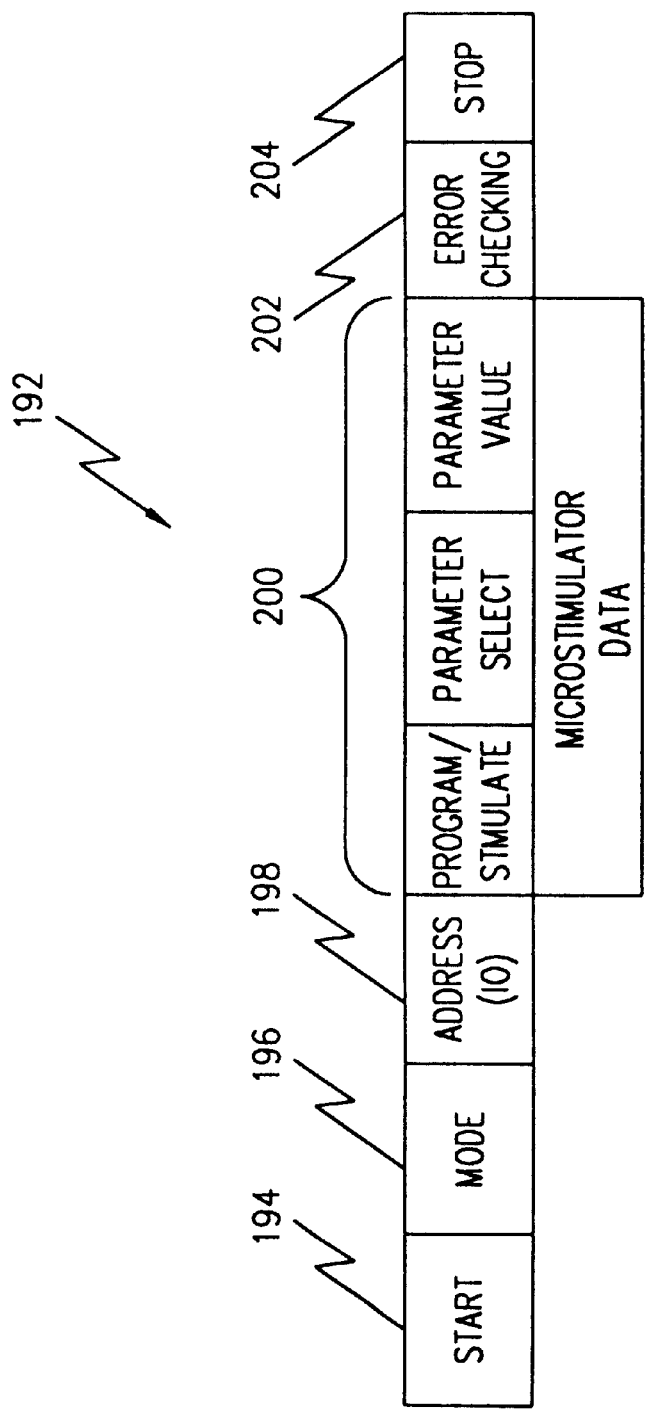
FIG. 4 is a simplified diagram showing the basic format of data messages for commanding/interrogating the implanted microstimulators, microsensors and microtransponders which form a portion of the present invention.

FIG. 4 shows the basic format of an exemplary message 192 for communicating with the aforementioned battery-powered devices 100, all of which are preconfigured with an address (ID), preferably unique to that device, in their identification storage 108 to operate in one or more of the following modes (1) for nerve stimulation, i.e., as a microstimulator, (2) for biological parameter monitoring, i.e., as a microsensor, and/or (3) for retransmitting received signals after reformatting to other implanted devices, i.e., as a microtransponder. The command message 192 is primarily comprised of a (1) start portion 194 (one or more bits to signify the start of the message and to synchronize the bit timing between transmitters and receivers, (2) a mode portion 196 (designating the operating mode, e.g., microstimulator, microsensor, microtransponder, or group mode), (3) an address (ID) portion 198 (corresponding to either the identification address 108 or a programmed group ID), (4) a data field portion 200 (containing command data for the prescribed operation), (5) an error checking portion 202 (for ensuring the validity of the message 192, e.g., by use of a parity bit), and (6) a stop portion 204 (for designating the end of the message 192). The basic definition of these fields are shown below in Table III. Using these definitions, each device can be separately configured, controlled and/or sensed as part of a system for controlling one or more neural pathways within a patient's body.

TABLE III

Message Data Fields

| MODE | ADDRESS (ID) |
|---|---|
| 00 = Stimulator | 8 bit identification address |
| 01 = Sensor | 8 bit identification address |
| 02 = Transponder | 4 bit identification address |
| 03 = Group | 4 bit group identification address |

| Data Field Portion | |
|---|---|
| Program/Stimulate | = select operating mode |
| Parameter/ Preconfiguration Select | = select programmable parameter in program mode or preconfigured stimulation or sensing parameter in other modes |
| Parameter Value | = program value |

Additionally, each device 100 can be programmed with a group ID (e.g., a 4 bit value) which is stored in its configuration data storage 132. When a device 100, e.g., a microstimulator, receives a group ID message that matches its stored group ID, it responds as if the message was directed to its identification address 108. Accordingly, a plurality of microstimulators, e.g., 100a and 100b, can be commanded with a single message. This mode is of particular use when precise timing is desired among the stimulation of a group of nerves.

The following describes exemplary commands, corresponding to the command message 192 of FIG. 4, which demonstrate some of the remote control/sensing capabilities of the system of devices which comprise the present invention:

Write Command—Set a microstimulator/microsensor specified in the address field 198 to the designated parameter value.

Group Write Command—Set the microstimulators/microsensors within the group specified in the address field 198 to the designated parameter value.

Stimulate Command—Enable a sequence of drive pulses from the microstimulator specified in the address field 198 according to previously programmed and/or default values.

Group Stimulate Command—Enable a sequence of drive pulses from the microstimulators within the group specified in the address field 198 according to previously programmed and/or default values.

Unit Off Command—Disable the output of the microstimulator specified in the address field 198.

Group Stimulate Command—Disable the output of the microstimulators within the group specified in the address field 198.

Read Command—Cause the microsensor designated in the address field 198 to read the previously programmed and/or default sensor value according to previously programmed and/or default values.

Read Battery Status Command—Cause the microsensor designated in the address field 198 to return its battery status.

Define Group Command—Cause the microstimulator/microsensor designated in the address field 198 to be assigned to the group defined in the microstimulator data field 200.

Set Telemetry Mode Command—Configure the microtransponder designated in the address field 198 as to its input mode (e.g., AC magnetic, sonic, etc.), output mode (e.g., AC magnetic, sonic, etc.), message length, etc.

Status Reply Command—Return the requested status/sensor data to the requesting unit, e.g., the SCU.

Download Program Command—Download program/safe harbor routines to the device, e.g., SCU, microstimulator, etc., specified in the address field 198.

Figure 5:
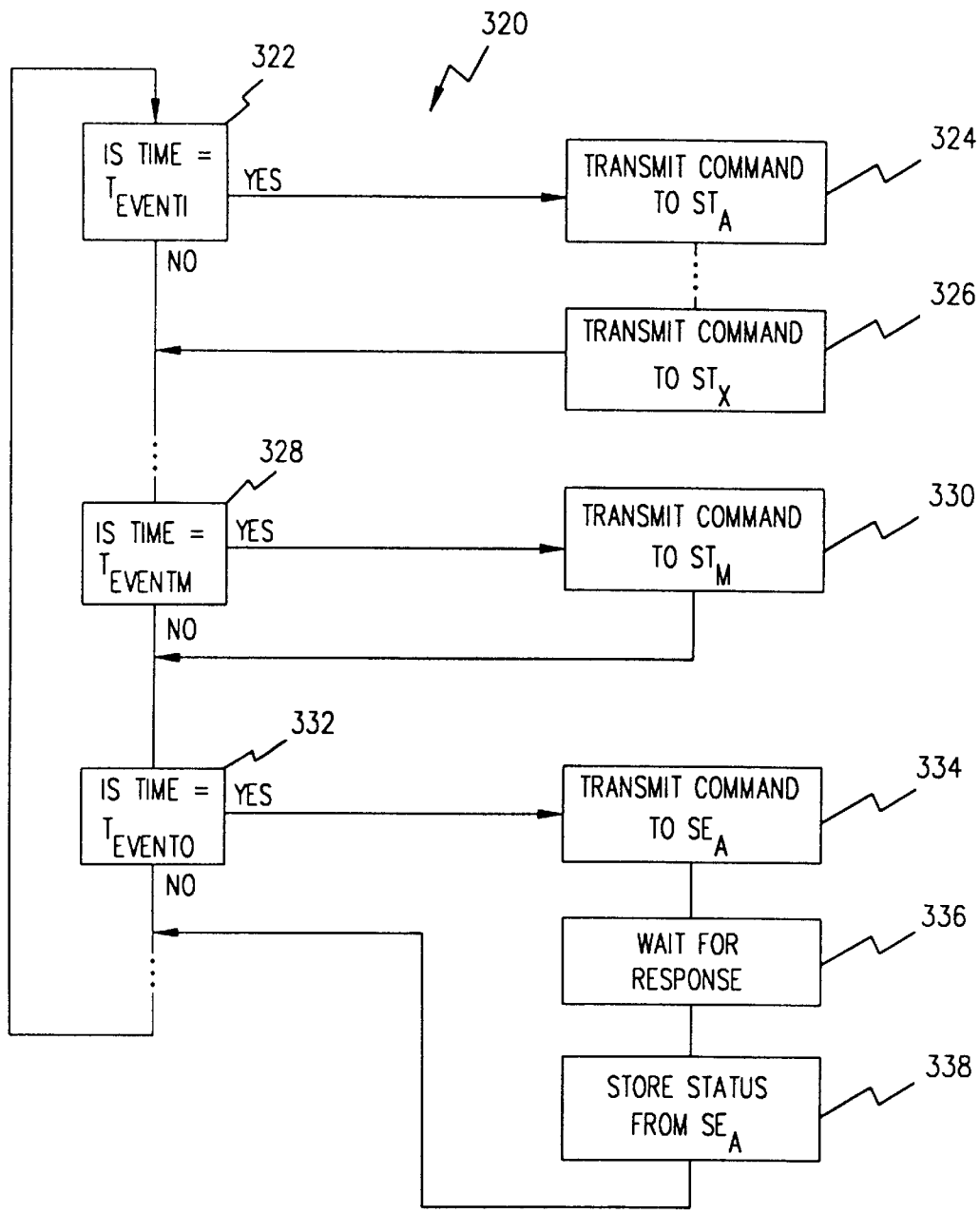
FIG. 5 shows an exemplary flow chart of the use of the present system in an open loop mode for controlling/monitoring a plurality of implanted devices, e.g., microstimulators, microsensors.

FIG. 5 shows a block diagram of an exemplary open loop control program, i.e., a task scheduler 320, for controlling/monitoring a body function/parameter. In this process, the programmable controller 308 is responsive to the clock 312 (preferably crystal controlled to thus permit real time scheduling) in determining when to perform any of a plurality of tasks. In this exemplary flow chart, the programmable controller 308 first determines in block 322 if is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g, stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). Is so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process can be used where the SCU 302 periodically interrogates each implantable device 100 to determine its battery status.

Figure 6:
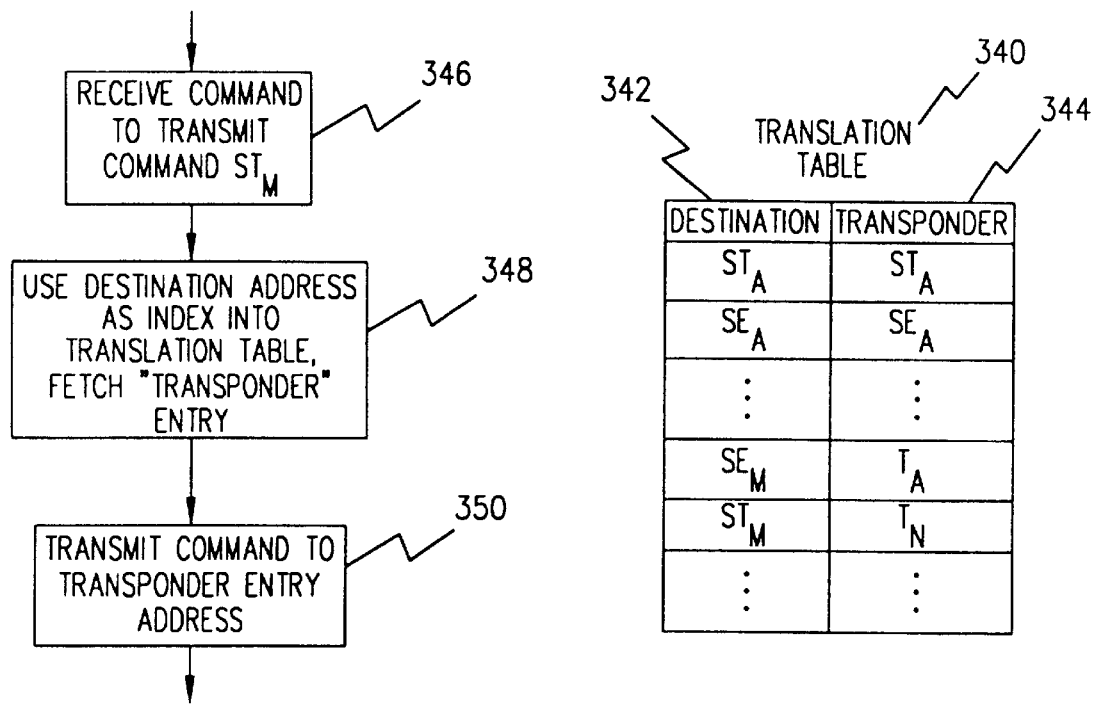
FIG. 6 shows a flow chart of the optional use of a translation table for communicating with microstimulators and/or microsensors via microtransponders.

FIG. 6 shows an exemplary use of an optional translation table 340 for communicating between the SCU 302 and microstimulators, e.g., 100a, and/or microsensors, e.g., 100c, via microtransponders, e.g., 100d. A microtransponder, e.g., 100d, is used when the communication range of the SCU 302 is insufficient to reliably communicate with other implanted devices 100. In this case, the SCU 302 instead directs a data message, i.e., a data packet, to an intermediary microtransponder, e.g., 100d, which retransmits the data packet to a destination device 100. In an exemplary implementation, the translation table 340 contains pairs of corresponding entries, i.e., first entries 342 corresponding to destination addresses and second entries 344 corresponding to the intermediary microtransponder addresses. When the SCU 302 determines, e.g., according to a timed event designated in the program storage 310, that a command is to be sent to a designated destination device (see block 346), the SCU 302 searches the first entries 342 of the translation table 340, for the destination device address, e.g., $ST_M$. The SCU 302 then fetches the corresponding second table entry 344 in block 348 and transmits the command to that address. When the second table entry 344 is identical to its corresponding first table entry 342, the SCU 302 transmits commands directly to the implanted device 100. However, when the second table entry 344, e.g., $T_N$, is different from the first table entry 342, e.g., $ST_M$, the SCU 302 transmits commands via an intermediary microtransponder, e.g., 100d. The use of the translation table 340 is optional since the intermediary addresses can, instead, be programmed directly into a control program contained in the program storage 310. However, it is preferable to use such a translation table 340 in that communications can be redirected on the fly by just reprogramming the translation table 340 to take advantage of implanted transponders as required, e.g., if communications should degrade and become unreliable. The translation table 340 is preferably contained in programmable memory, e.g., RAM or EPROM, and can be a portion of the program storage 310. While the translation table 340 can be remotely programmed, e.g., via a modulated signal from the clinician's programmer 172, it is also envisioned that the SCU 302 can reprogram the translation table 340 if the communications degrade.

Figure 7:
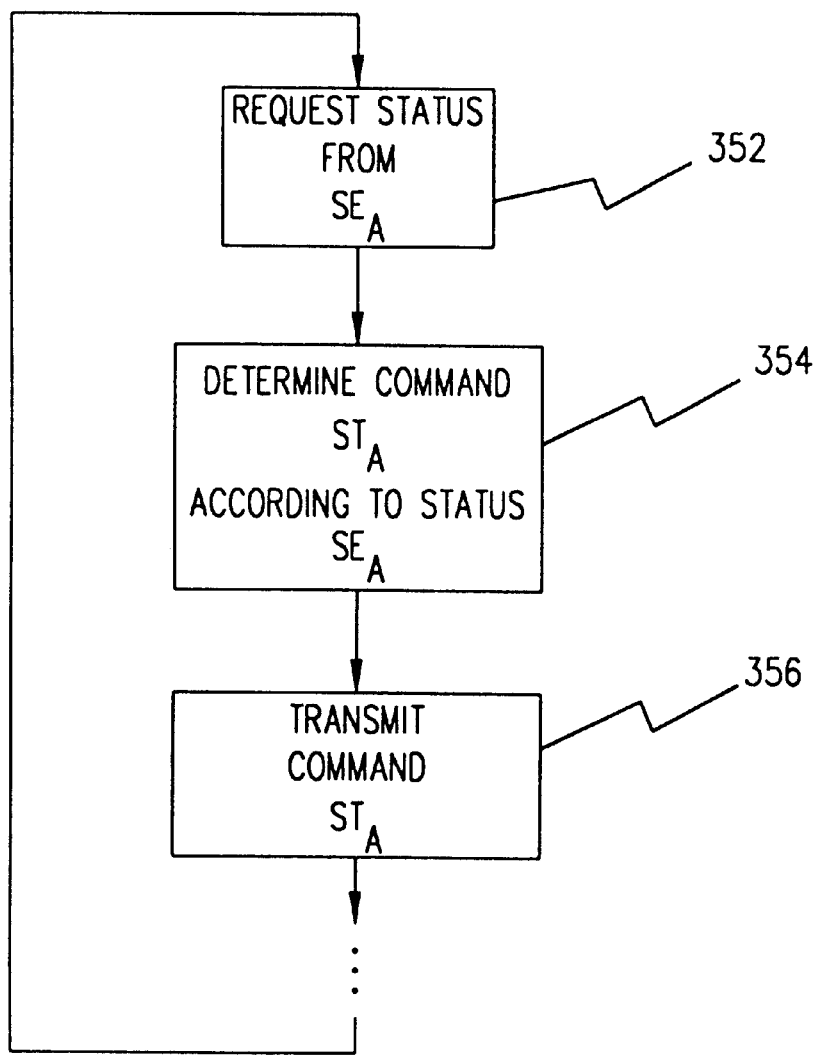
FIG. 7 shows a simplified flow chart of the use of: closed loop control of a microstimulator by altering commands from the system control unit in response to status data received from a microsensor.

FIG. 7 is an exemplary block diagram showing the use of the system of the present invention to perform closed loop control of a body function. In block 352, the SCU 302 requests status from microsensor A ($SE_A$) The SCU 302, in block 354, then determines whether a current command given to a microstimulator is satisfactory and, if necessary, determines a new command and transmits the new command to the microstimulator A in block 356. For example, if microsensor A ($SE_A$) is reading a voltage corresponding to a pressure generated by the stimulation of a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (position, integral, derivative (PID)) control are preferably program controlled by the SCU 302 according to the control program contained in program storage 310.

Figure 8:
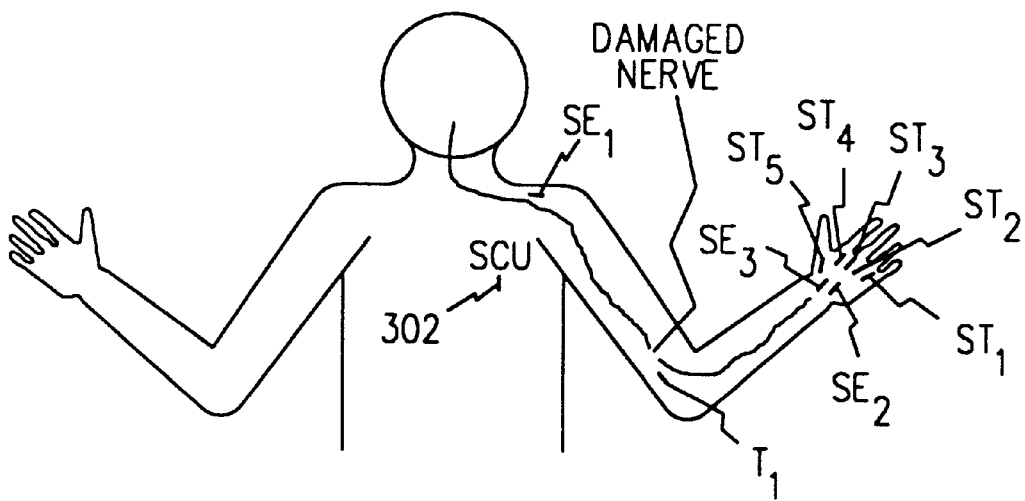
FIG. 8 shows an exemplary injury, i.e., a damaged nerve, and the placement of a plurality of implanted devices, i.e., microstimulators, microsensors and a microtransponder under control of the system control unit for "replacing" the damaged nerve.

FIG. 8 shows an exemplary injury treatable by embodiments of the present system 300. In this exemplary injury, the neural pathway has been damaged, e.g, severed, just above the a patient's left elbow. The goal of this exemplary system is to bypass the damaged neural pathway to permit the patient to regain control of the left hand. An SCU 302 is implanted within the patient's torso to control plurality of stimulators, $ST_1$–$ST_5$, implanted proximate to the muscles respectively controlling the patient's thumb and fingers. Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 9:
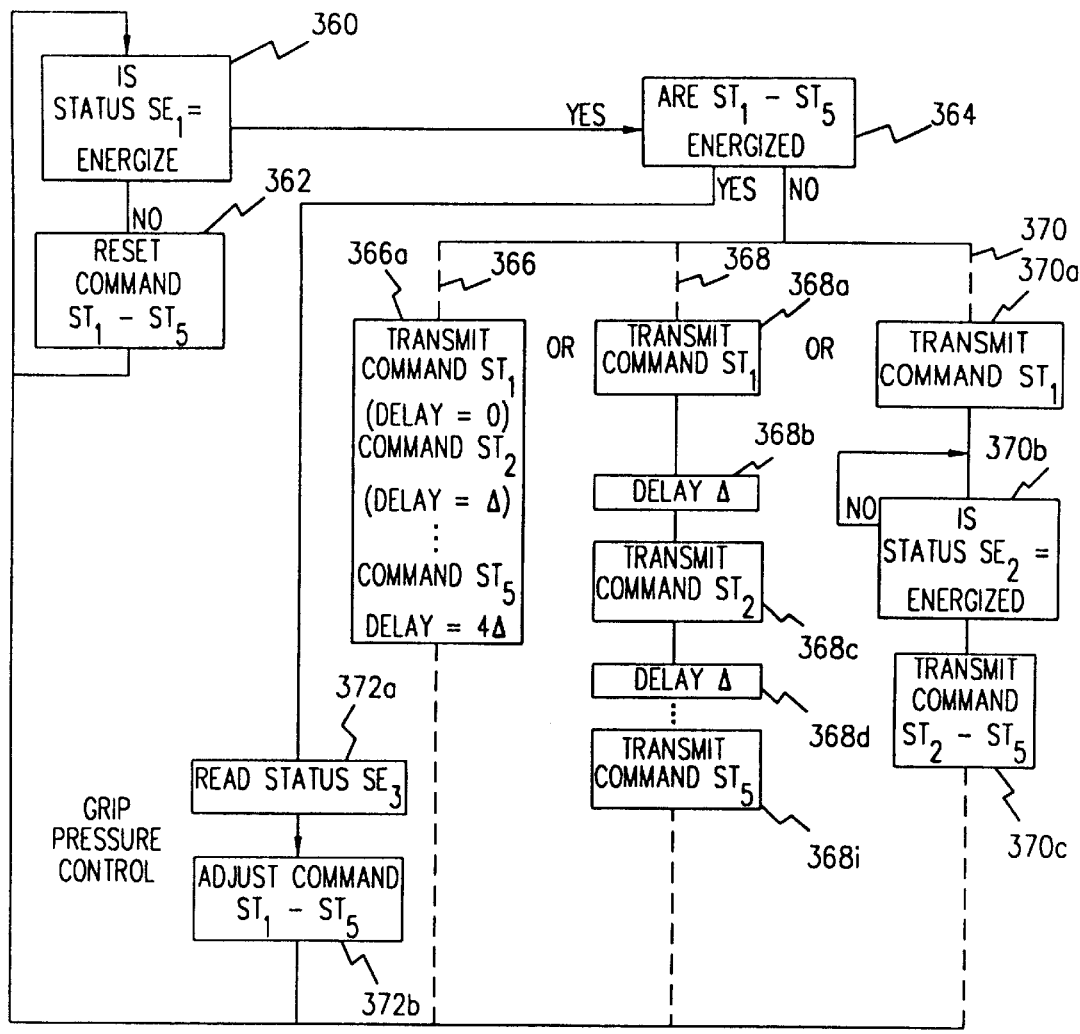
FIG. 9 shows a simplified flow chart of the control of the implanted devices of FIG. 8 by the system control unit.

FIG. 9 shows an exemplary flow chart for the operation of the SCU 302 in association with the implanted devices in the exemplary system of FIG. 8. In block 360, the SCU 302 interrogates microsensor 1 ($SE_1$) to determine if the patient is requesting actuation of his fingers. If not, a command is transmitted in block 362 to all of the stimulators ($ST_1$–$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$–$ST_5$ are currently energized, i.e., generating a sequence of drive pulses. If not, the SCU 302 executes instructions to energize the stimulators. In a first optional path 366, each of the stimulators are simultaneously (subject to formatting and transmission delays) commanded to energize in block 366a. However, the command signal given to each one specifies a different start delay time (using the BON parameter). Accordingly, there is a stagger between the actuation/closing of each finger.

In a second optional path 368, the microstimulators are consecutively energized by a delay Δ. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor ($SE_2$), before actuating the remaining stimulators ($ST_2$–$ST_5$) in block 370c. This implementation could provide more coordinated movement in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$–$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the parent application, it was shown that such a sensor 186 could be used to disable the operation of an implanted device 100, e.g., to stop the operation of such devices in an emergency situation, in response to a DC magnetic field, preferably from an externally positioned safety magnet 187. A further implementation is disclosed herein. The magnetic sensor 186 can be implemented using various devices. Exemplary of such devices are devices manufactured by Nonvolatile Electronics, Inc. (e.g., their AA, AB, AC, AD, or AG series), Hall effect sensors, and subminiature reed switches. Such miniature devices are configurable to be placed within the housing of the disclosed SCU 302 and implantable devices 100. While essentially passive magnetic sensors, e.g., reed switches, are possible, the remaining devices include active circuitry that consumes power during detection of the DC magnetic field. Accordingly, it is preferred that controller circuitry 302 periodically, e.g., once a second, provide power the magnetic sensor 186 and sample the sensor's output signal 374 during that sampling period.

In a preferred implementation of the SCU 302, the programmable controller 308 is a microcontroller operating under software control wherein the software is located within the program storage 310. The SCU 302 preferably includes an input 376, e.g., a non maskable interrupt (NMI), which causes a safe harbor subroutine 378, preferably located within the program storage 310, to be executed. Additionally, failure or potential failure modes, e.g., low voltage or over temperature conditions, can be used to cause the safe harbor subroutine 378 to be executed. Typically, such a subroutine could cause a sequence of commands to be transmitted to set each microstimulator into a safe condition for the particular patient configuration, typically disabling each microstimulator. Alternatively, the safe harbor condition could be to set certain stimulators to generate a prescribed sequence of drive pulses. Preferably, the safe harbor subroutine 378 can be downloaded from an external device, e.g., the clinician's programmer 172, into the program storage 310, a nonvolatile storage device. Additionally, it is preferable that, should the programmable contents of the program storage be lost, e.g., from a power failure, a default safe harbor subroutine be used instead. This default subroutine is preferably stored in nonvolatile storage that is not user programmable, e.g., ROM, that is otherwise a portion of the program storage 310. This default subroutine is preferably general purpose and typically is limited to commands that turn off all potential stimulators.

Alternatively, such programmable safe harbor subroutines 378 can exist in the implanted stimulators 100. Accordingly, a safe harbor subroutine could be individually programmed into each microstimulator that is customized for the environments of that microstimulator and a safe harbor subroutine for the SCU 302 could then be designated that disables the SCU 302, i.e., causes the SCU 302 to not issue subsequent commands to other implanted devices 100.

Figure 10A:
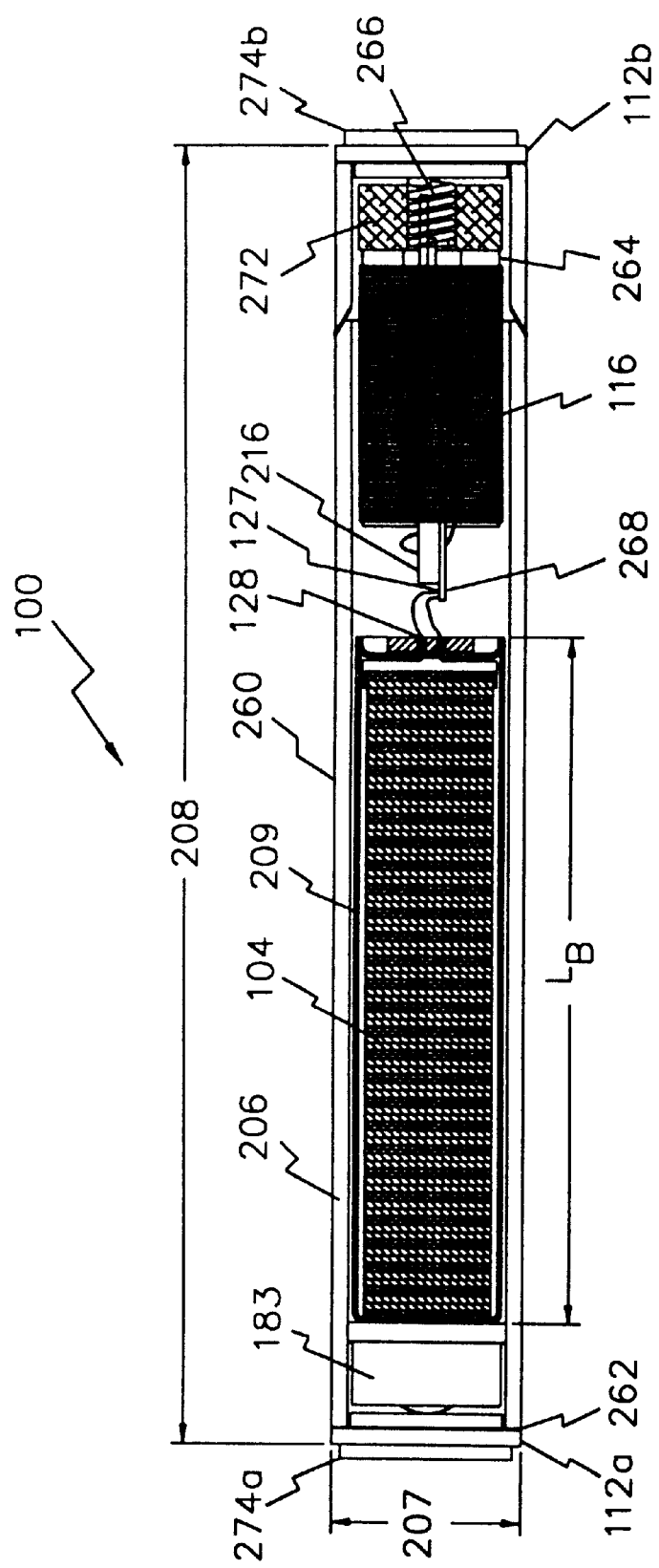
FIGS. 10A and 10BD show two side cutaway views of the presently preferred embodiment of an implantable ceramic tube suitable for the housing the system control unit and/or microstimulators and/or microsensors and/or microtransponders.
Figure 10B:
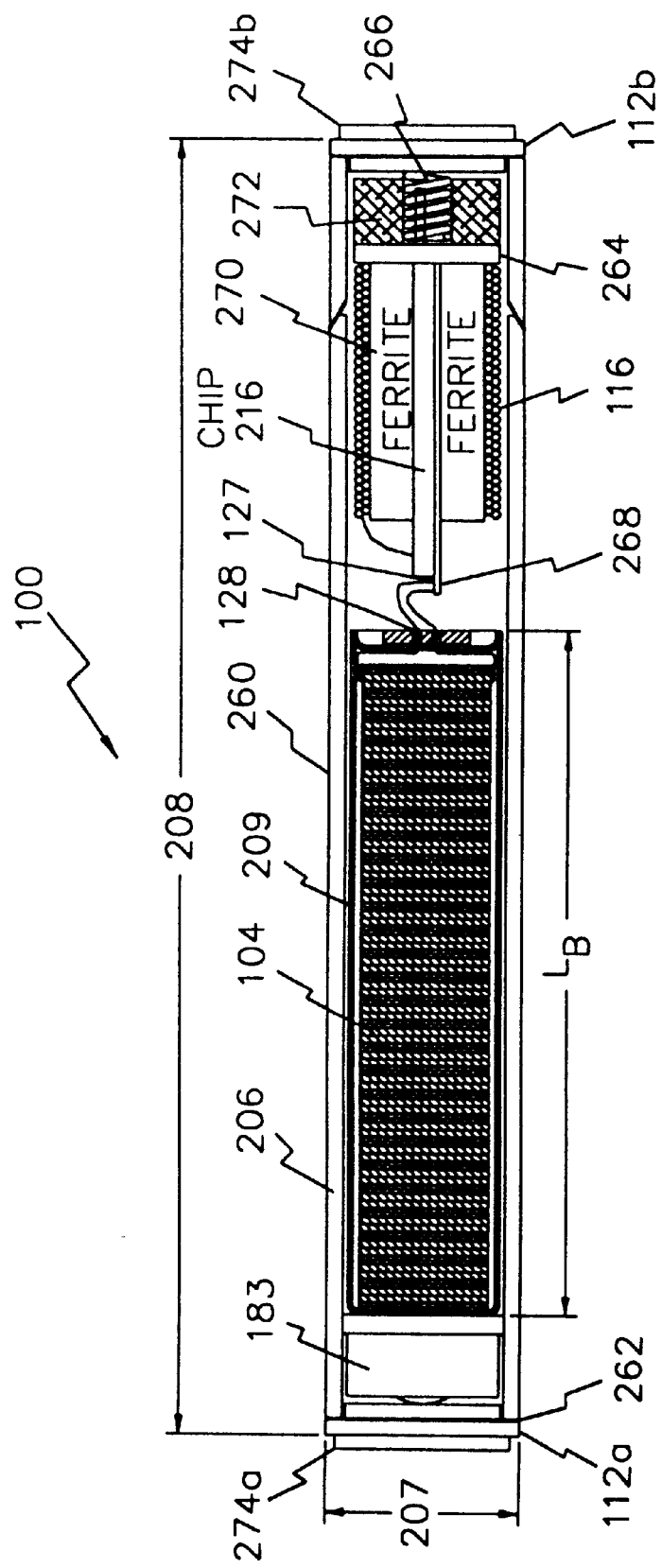

FIGS. 10A and 10BD show two side cutaway views of the presently preferred construction of the sealed housing 206, the battery 104 and the circuitry (implemented on one or more IC chips 216 to implement electronic portions of the SCU 302) contained within. In this presently preferred construction, the housing 206 is comprised of an insulating ceramic tube 260 brazed onto a first end cap forming electrode 112a via a braze 262. At the other end of the ceramic tube 260 is a metal ring 264 that is also brazed onto the ceramic tube 260. The circuitry within, i.e., a capacitor 183 (used when in a microstimulator mode), battery 104, IC chips 216, and a spring 266 is attached to an opposing second end cap forming electrode 112b. A drop of conductive epoxy is used to glue the capacitor 183 to the end cap 112a and is held in position by spring 266 as the glue takes hold. Preferably, the IC chips 216 are mounted on a circuit board 268 over which half circular longitudinal ferrite plates 270 are attached. The coil 116 is wrapped around the ferrite plates 270 and attached to IC chips 216. A getter 272, mounted surrounding the spring 266, is preferably used to increase the hermeticity of the SCU 302 by absorbing water introduced therein. An exemplary getter 272 absorbs 70 times its volume in water. While holding the circuitry and the end cap 112b together, one can laser weld the end cap 112b to the ring 264. Additionally, a platinum, iridium, or platinum-iridium disk or plate 274 is preferably welded to the end caps of the SCU 302 to minimize the impedance of the connection to the body tissue.

An exemplary battery 104 is described more fully below in connection with the description of FIG. 11. Preferably, the battery 104 is made from appropriate materials so as to provide a power capacity of at least 1 microwatt-hour, preferably constructed from a battery having an energy density of about 240 mW-Hr/cm$^3$. A Li—I battery advantageously provides such an energy density. Alternatively, an Li—I—Sn battery provides an energy density up to 360 mW-Hr/cm$^3$. Any of these batteries, or other batteries providing a power capacity of at least 1 microwatt-hour may be used with implanted devices of the present invention.

The battery voltage V of an exemplary battery is nominally 3.6 volts, which is more than adequate for operating the CMOS circuits preferably used to implement the IC chip(s) 216, and/or other electronic circuitry, within the SCU 302. The battery voltage V, in general, is preferably not allowed to discharge below about 2.55 volts, or permanent damage may result. Similarly, the battery 104 should preferably not be charged to a level above about 4.2 volts, or else permanent damage may result. Hence, a charging circuit 122 (discussed in the parent application) is used to avoid any potentially damaging discharge or overcharge.

The battery 104 may take many forms, any of which may be used so long as the battery can be made to fit within the small volume available. As previously discussed, the battery 104 may be either a primary battery or a rechargeable battery. A primary battery offers the advantage of a longer life for a given energy output but presents the disadvantage of not being rechargeable (which means once its energy has been used up, the implanted device no longer functions). However, for many applications, such as one-time-only muscle rehabilitation regimens applied to damaged or weakened muscle tissue, the SCU 302 and/or devices 100 need only be used for a short time (after which they can be explanted and discarded, or simply left implanted as benign medical devices). For other applications, a rechargeable battery is clearly the preferred type of energy choice, as the tissue stimulation provided by the microstimulator is of a recurring nature.

The considerations relating to using a rechargeable battery as the battery 104 of the implantable device 100 are presented, inter alia, in the book, *Rechargeable Batteries, Applications Handbook*, EDN Series for Design Engineers, Technical Marketing Staff of Gates Energy Products, Inc. (Butterworth-Heinemann 1992). The basic considerations for any rechargeable battery relate to high energy density and long cycle life. Lithium based batteries, while historically used primarily as a nonrechargeable battery, have in recent years appeared commercially as rechargeable batteries. Lithium-based batteries typically offer an energy density of from 240 mW-Hr/cm$^3$ to 360 mW-Hr/cm$^3$. In general, the higher the energy density the better, but any battery construction exhibiting an energy density resulting in a power capacity greater than 1 microwatt-hour is suitable for the present invention.

One of the more difficult hurdles facing the use of a battery 104 within the SCU 302 relates to the relatively small size or volume inside the housing 206 within which the battery must be inserted. A typical SCU 302 made in accordance with the present invention is no larger than about 60 mm long and 8 mm in diameter, preferably no larger than 60 mm long and 6 mm in diameter, and includes even smaller embodiments, e.g., 15 mm long with an O.D. of 2.2 mm (resulting in an I.D. of about 2 mm). When one considers that only about ¼ to ½ of the available volume within the device housing 206 is available for the battery, one begins to appreciate more fully how little volume, and thus how little battery storage capacity, is available for the SCU 302.

Figure 11:
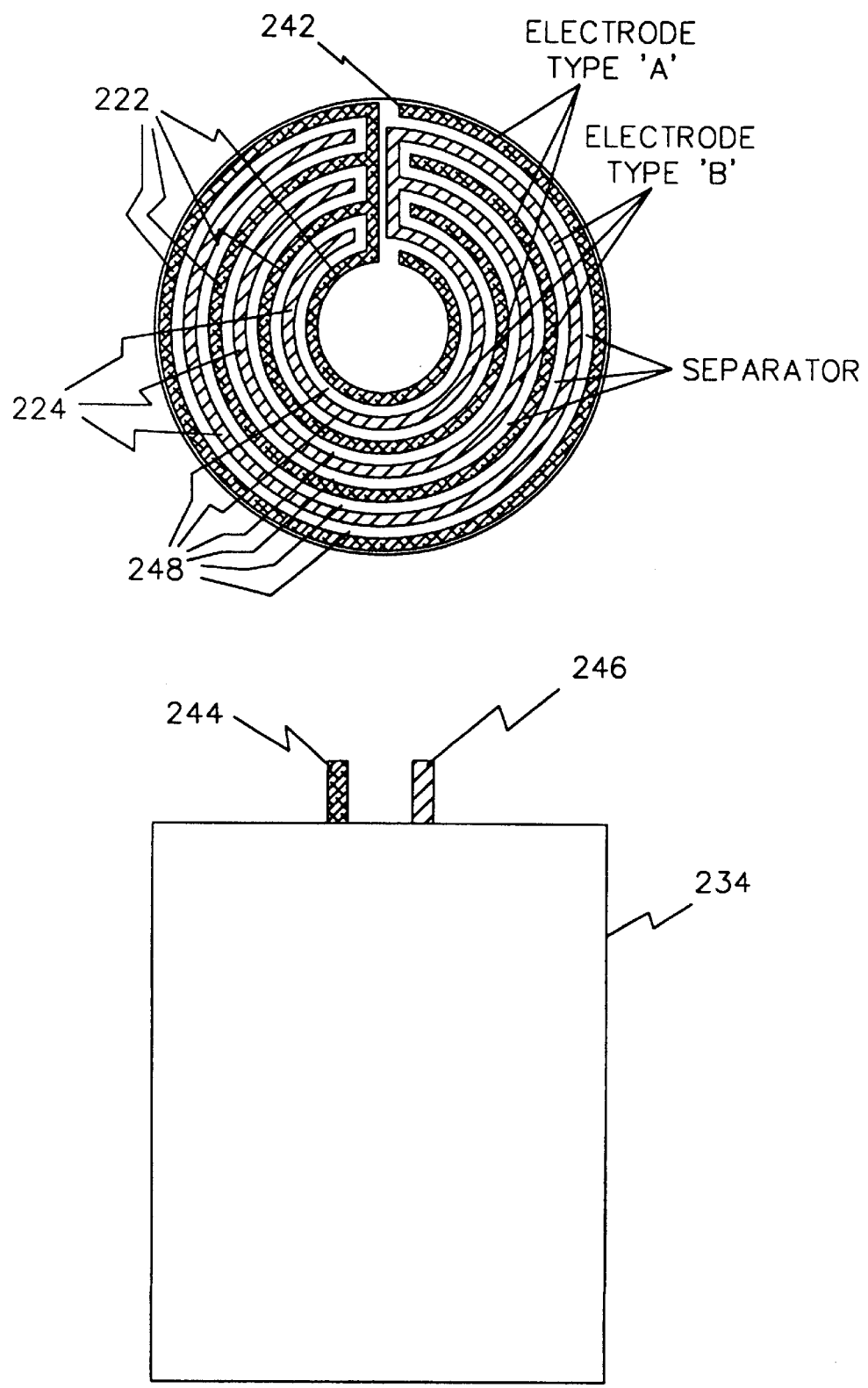
FIG. 11 illustrates an exemplary battery suitable for powering the implantable devices which comprise the components of the present invention.

FIG. 11 shows an exemplary battery 104 typical of those disclosed in the parent application. Specifically, a parallel-connected cylindrical electrode embodiment is shown where each cylindrical electrode includes a gap or slit 242; with the cylindrical electrodes 222 and 224 on each side of the gap 242 a common connection point for tabs 244 and 246 which serve as the electrical terminals for the battery. The electrodes 222 and 224 are separated by a suitable separator 248. The gap 242 minimizes the flow of eddy currents in the electrodes. For this embodiment, there are four concentric cylindrical electrodes 222, the outer one (largest diameter) of which may function as the battery case 234, and three concentric electrodes 224 interleaved between the electrodes 222, with six concentric cylindrical separator layers 248 separating each electrode 222 or 224 from the adjacent electrodes.

Accordingly, a preferred embodiment of the present invention is comprised of an implanted SCU 302 and a plurality of implanted devices 100, each of which contains its own rechargeable battery 104. As such, a patient is essentially independent of any external apparatus between battery chargings (which generally occur no more often than once an hour). However, for some treatment regimen, it may be adequate to use a power supply analogous to that described in U.S. Pat. No. 5,324,316 that only provides power while an external AC magnetic field is being provided, e.g., from charger 118. Additionally, it may be desired, e.g., from a cost standpoint, to implement the SCU 302 as an external device, e.g., within a watch-shaped housing that can be attached to a patient's wrist in a similar manner to the patient control unit 174.

Figure 12:
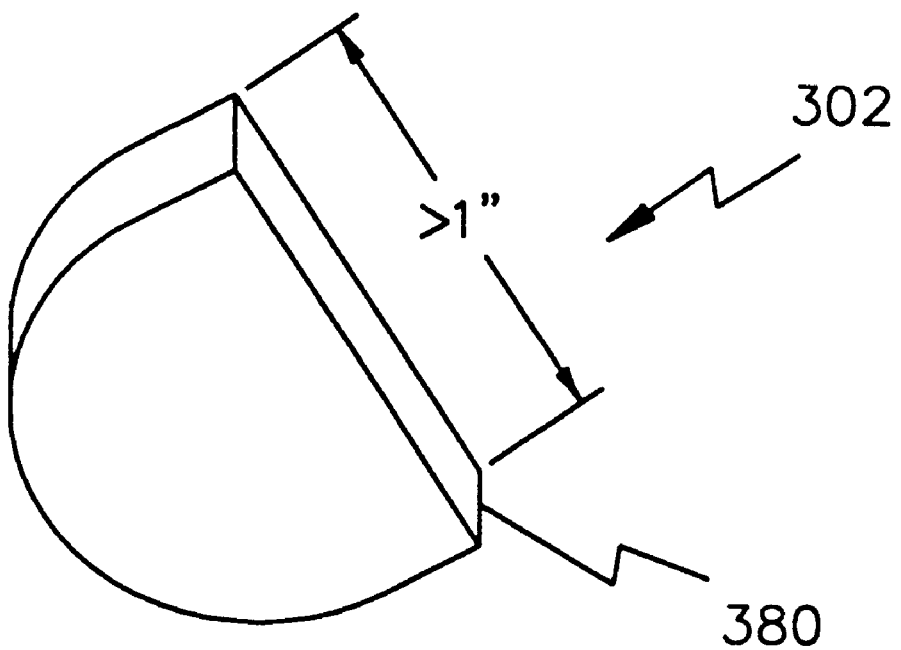
FIG. 12 shows an exemplary housing suitable for an implantable SCU having a battery enclosed within that has a capacity of at least 1 watt-hour.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 watt-hour is preferred. While a primary battery is possible, it is preferable that a rechargeable battery be used. Such larger batteries will require a larger volume and accordingly, cannot be placed in the injectable housing described above. However, a surgically implantable device within a larger sealed housing, e.g., having at least one dimension in excess of 1 inch, will serve this purpose when used in place of the previously discussed injectable housing 206. FIG. 12 shows an exemplary implantable housing 380 suitable for such a device.

While the invention herein disclosed has been described by means of specific embodiments and applications thereof, numerous modifications and variations could be made thereto by those skilled in the art without departing from the scope of the invention set forth in the claims. For example, a system including multiple SCUs, e.g., one external and one internal, is considered to be within the scope of the present invention. Additionally, while the use of a single communication channel for communication between one or more SCUs and the other implanted devices has been described, a system implemented using multiple communication channels, e.g., a first sonic channel at a first carrier frequency and a second sonic channel at a second carrier frequency, is also considered to be within the scope of the present invention.

We claim:

1. A system for stimulating body tissue internal to a patient's body, said system comprising:

a plurality of addressable devices each comprised of a housing having an axial dimension of less than 60 mm and a lateral dimension of less than 6 mm and configured for injection into said patient's body, each of said devices including circuitry operable in accordance with one or more controllable operating parameters to stimulate body tissue and including a battery having a capacity of at least one microwatt-hour;

each of said addressable devices including an address storage means, a data signal transmitter and a data signal receiver; and a system control unit comprised of a housing configured for implantation in said patient's body for controlling said controllable operating parameters, said system control unit comprising:

a signal transmitter in said control unit housing for transmitting command signals including address information identifying at least one of said addressable devices and operating parameter information for controlling an operating parameter of the identified addressable device;

a programmable controller in said control unit housing for producing command signals for transmission by said control unit signal transmitter to said addressable devices;

a power supply in said control unit housing for providing operating power to said control unit signal transmitter, signal receiver, and programmable controller; and wherein said power supply has a capacity of at least one watt-hour.

2. The system of claim 1 wherein said control unit further includes storage means storing a program defining a sequence of operations; and wherein said programmable controller operates to execute the sequence of operations defined by said program.

3. The system of claim 2 further including a programmer disposed external to said patient's body for producing program information; and means responsive to said externally produced program information for modifying the content of said storage means.

4. The system of claim 3 wherein said program storage means includes an alterable portion and a nonalterable portion; and wherein said nonalterable portion stores a default program.

5. The system of claim 3 wherein said means responsive to said program information includes means for producing a modulated alternating magnetic field.

6. The system of claim 1 wherein at least one of said addressable devices is operable in one or more modes including a stimulator mode, a sensor mode, and a transponder mode; and wherein said addressable device is responsive to a command signal from said control unit transmitter defining one or more operating modes.

7. The system of claim 1 wherein at least one of said addressable devices includes means responsive to a command signal for transmitting data signals via said device signal transmitter; and wherein said programmable controller is responsive to received data signals for defining command signals for transmission by said control unit signal transmitter.

8. The system of claim 1 wherein said control unit power supply comprises a battery; and further including:

an internal coil and a charging circuit disposed in said control unit housing for supplying a charging current to said battery.

9. The system of claim 8 further including means for generating an alternating magnetic field outside of said patient's body for supplying energy to said charging circuit via said internal coil.

10. The system of claim 1 wherein said addressable devices each contains an electrode extending externally of the device housing; and wherein said device circuitry is operable to supply a sequence of drive pulses to said electrode.

11. The system of claim 1 wherein at least one of said addressable devices includes a battery for supplying power to said circuitry.

12. The system of claim 11 wherein at least one addressable device signal transmitter transmits status signals indicative of the charge state of the battery therein.

* * * * *

UNITED STATES PATENT AND TRADEMARK OFFICE
CERTIFICATE OF CORRECTION

PATENT NO. : 6,208,894 B1
DATED : March 27, 2001
INVENTOR(S) : Schulman et al.

It is certified that error appears in the above-identified patent and that said Letters Patent is hereby corrected as shown below:

Title page,
Item [60], Related U.S. Application Data, should read as follows:
-- [60]  Provisional application No. 60/042,447, filed on Mar. 27, 1997, and provisional application No. 60/039,164, filed on Feb. 26, 1997.

[63]  Continuation-in-part of application No. 09/030,106, filed on Feb. 25, 1998, now Pat. No. 6,185,452. --

Column 1,
Lines 5-10, should read as follows:
-- This application is a continuation-in-part of U.S. patent application Ser. No. 09/030,106, filed Feb. 25, 1998, which in turn claims the benefit of U.S. Provisional Application Ser. No. 60/039,164, filed Feb. 26, 1997. Additionally, the present application claims the benefit of U.S. Provisional Application Ser. No. 60/042,447, filed Mar. 27, 1997. --

Column 3,
Line 31, should read as follows:
-- FIGS. 10A and 10B show two side cutaway views of the --

Column 7,
Line 20, should read as follows:
-- mode of the sensor circuitry 188 is remotely programmable --

Column 12,
Line 41, should read as follows:
-- FIGS. 10A and 10B show two side cutaway views of the --

Signed and Sealed this

Fifth Day of April, 2005

JON W. DUDAS
*Director of the United States Patent and Trademark Office*